United States Patent
Zhang et al.

(10) Patent No.: US 10,406,153 B2
(45) Date of Patent: Sep. 10, 2019

(54) PROCESS FOR THE PREPARATION OF BENZHYDROCODONE HYDROCHLORIDE

(71) Applicant: Noramco, Inc., Wilmington, DE (US)

(72) Inventors: Wen-Chun Zhang, Bogart, GA (US); Bruce P. Johnson, Athens, GA (US)

(73) Assignee: Noramco, Inc., Wilmington, DE (US)

( * ) Notice: Subject to any disclaimer, the term of this patent is extended or adjusted under 35 U.S.C. 154(b) by 0 days.

(21) Appl. No.: 15/692,430

(22) Filed: Aug. 31, 2017

(65) Prior Publication Data

US 2018/0055836 A1 Mar. 1, 2018

Related U.S. Application Data

(60) Provisional application No. 62/382,143, filed on Aug. 31, 2016, provisional application No. 62/472,612, filed on Mar. 17, 2017.

(51) Int. Cl.
| | | |
|---|---|---|
| *A61K 31/485* | (2006.01) | |
| *C07D 489/04* | (2006.01) | |
| *A61P 23/00* | (2006.01) | |

(52) U.S. Cl.
CPC ............ *A61K 31/485* (2013.01); *A61P 23/00* (2018.01); *C07D 489/04* (2013.01); *C07B 2200/13* (2013.01)

(58) Field of Classification Search
CPC .................................................. A61K 31/485
See application file for complete search history.

(56) References Cited

U.S. PATENT DOCUMENTS

| | | | |
|---|---|---|---|
| 1,731,152 A | 10/1929 | Schofp | |
| 7,348,430 B2 | 3/2008 | Likhotvorik et al. | |
| 8,461,137 B2 | 6/2013 | Mickle et al. | |
| 8,748,413 B2 | 6/2014 | Mickle et al. | |
| 8,759,368 B2 * | 6/2014 | Mickle | A61K 31/485 514/282 |
| 2016/0039837 A1 | 2/2016 | Heinrich et al. | |

FOREIGN PATENT DOCUMENTS

| | | | |
|---|---|---|---|
| WO | WO 2014/138740 | * | 9/2014 |
| WO | WO-2014/138740 A1 | | 9/2014 |

OTHER PUBLICATIONS

Small, L., et al., "The Addition of Organomagnesium Halides to Pseudocodeine Types IV. Nuclear-Substituted Morphine Derivatives" Journal of Organic Chemistry, 1938, p. 204, vol. 3.

* cited by examiner

*Primary Examiner* — Paul V Ward
(74) *Attorney, Agent, or Firm* — Alston & Bird, LLP

(57) ABSTRACT

The invention is directed to processes for the preparation of benzhydrocodone hydrochloride. More particularly, the invention is directed to processes for a one-pot synthesis of benzhydrocodone hydrochloride of improved yield and/or purity.

11 Claims, 1 Drawing Sheet

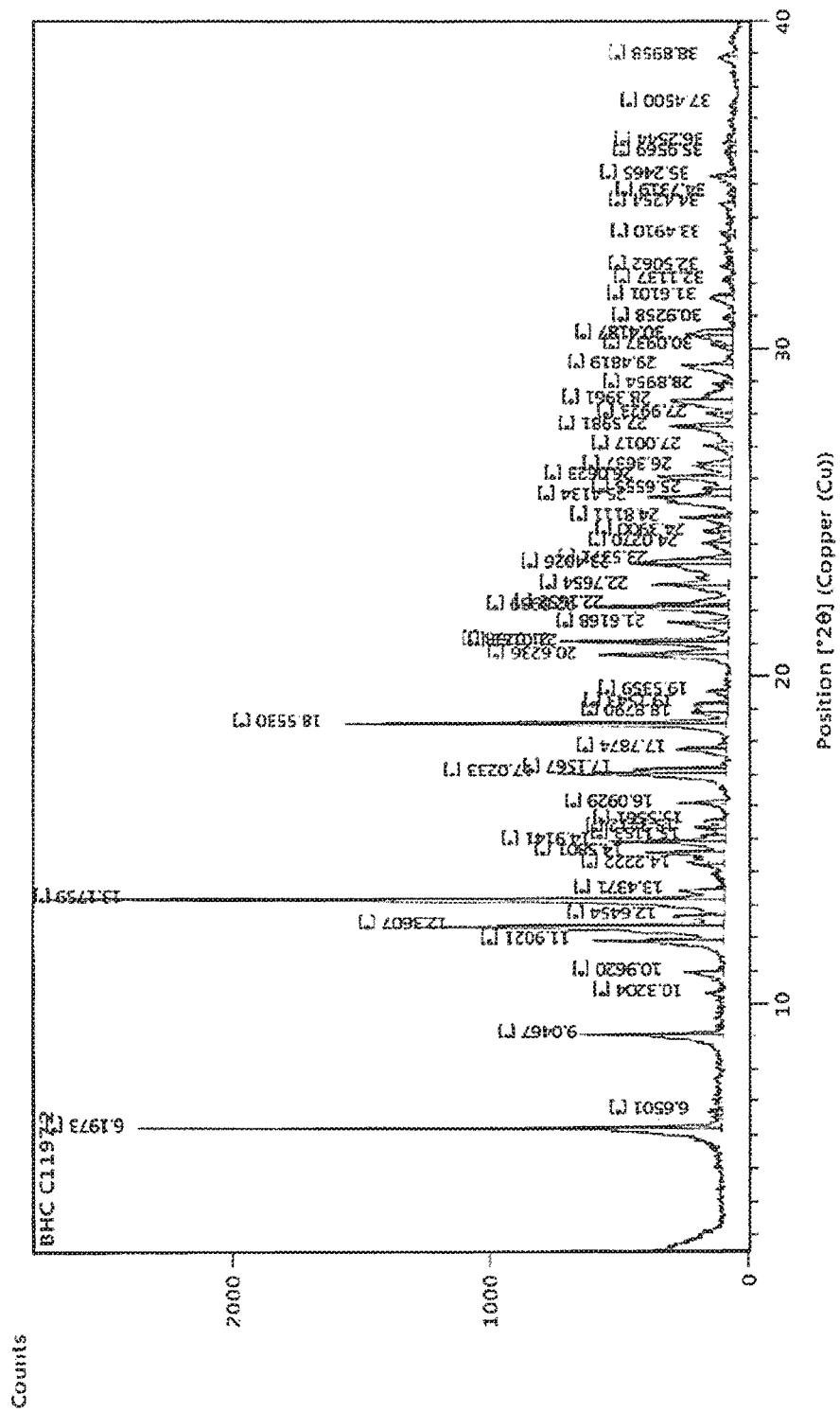

PROCESS FOR THE PREPARATION OF BENZHYDROCODONE HYDROCHLORIDE

CROSS-REFERENCE TO RELATED APPLICATIONS

This application claims the benefit of U.S. Provisional Application No. 62/382,143, filed Aug. 31, 2016, and U.S. Provisional Application No. 62/472,612, filed Mar. 17, 2017, the entireties of which are incorporated herein by reference.

FIELD OF THE INVENTION

The invention is directed to processes for the preparation of benzhydrocodone hydrochloride. More particularly, the invention is directed to processes for the one-pot synthesis of benzhydrocodone hydrochloride with improved yield and/or purity that meets all the active pharmaceutical ingredient (API) quality attributes without involving any additional purification step(s).

BACKGROUND OF THE INVENTION

Benzhydrocodone, also known as benzoate-hydrocodone, is an opioid prodrug of the morphinan class and having the following chemical structure:

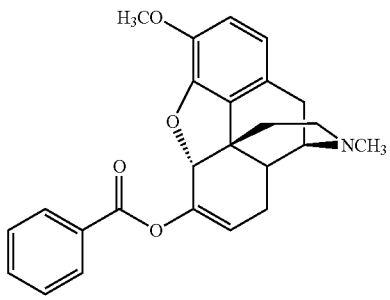 [SMILES: COc1ccc2c3c1O[C@H]1C(OC(=O)c4ccccc4)=CCC4[C@@H](C2)N(C)CC[C@@]341]

(hydrocodone coupled with benzoic acid).

Benzhydrocodone itself is inactive, but acts as a prodrug, producing hydrocodone upon cleavage of the benzoate portion of the molecule. Benzhydrocodone was designed to be an opioid analgesic with lower abuse potential.

SCHOFP, C., in U.S. Pat. No. 1,731,152, issued Oct. 8, 1929 describes a process for the manufacture of a derivative of dihydrocodeinone or its substitution products, including preparation of methiodide of benzoyl hydrocodeinone.

SMALL, L. et al., in Journal of Organic Chemistry, 1938, p. 204. Vol. 3 describes a process for the preparation of hydrocodone enol acetate by reacting hydrocodone with acetic anhydride in the presence of sodium acetate and heat.

LIKHOTVORIK, I., et al., in U.S. Pat. No. 7,348,430, issued Mar. 25, 2008, describe a process for the manufacture of dihydrothebaine, dihydrocodeinone enol acetate, hydrocodone, and analogs.

MICKLE, T., et al., in U.S. Pat. No. 8,461,137, issued Jun. 11, 2013, MICKLE, T., et al., in U.S. Pat. No. 8,748,413, issued Jun. 10, 2014, and MICKLE, T., et al., in U.S. Pat. No. 8,759,368, issued Jun. 24, 2014, describe compositions comprising aryl carboxylic acids chemically conjugated with hydrocodone to form prodrugs/compositions of hydrocodone, including benzoates and heteroaryl carboxylic acids.

HEINRICH, B. W., et al., in PCT Patent Publication WO 2014/138740 A1, published Sep. 12, 2014 (US Equivalent Patent Publication US 2016/0039837), describe pharmaceutically acceptable salts and polymorphic forms of hydrocodone benzoic acid enol ester and processes for making same.

There remains a need for a process for the preparation of benzhydrocodone hydrochloride that is suitable for large scale and/or commercial manufacture.

SUMMARY OF THE INVENTION

In one embodiment, the invention is directed to processes for the preparation of benzhydrocodone including the steps of:

(a) mixing benzoic anhydride, hydrocodone free base in an organic solvent to yield a reaction mixture;

(b) removing the organic solvent of the reaction mixture (prepared in step (a)), for example by distillation, optionally with $N_2$ or other inert gas sweep; and (c) heating the reaction mixture of step (b) to a temperature in the range of about 100° C. to about 200° C. to yield benzhydrocodone.

In some embodiments, the invention is directed to processes for the preparation of benzhydrocodone including the steps of:

(a) mixing benzoic anhydride, hydrocodone free base, and an organic solvent;

(b) removing a substantial portion of the organic solvent from the mixture, for example by distillation, optionally with $N_2$ or other inert gas sweep; and (c) heating the resulting mixture to a temperature in the range of about 100° C. to about 200° C.

In one embodiment, the invention is directed to a process for the preparation of benzhydrocodone hydrochloride including the steps of (Methods A & B):

(a) reacting hydrocodone free base with benzoic anhydride at a temperature in the range of from about 100° C. to about 200° C. to yield a reaction mixture (e.g., a syrupy or oily residue) including benzhydrocodone free base (which may include unreacted hydrocodone freebase and unreacted benzoic anhydride and benzoic acid);

(b) adding to the reaction mixture an organic solvent, and a solvent (e.g., acetone) which is miscible with both the organic solvent and water, to yield a first work-up mixture:

(c) adjusting the pH of the first work-up mixture to a pH in the range of from about pH 1.0 to about pH 5.0, wherein the pH is adjusted by addition of hydrochloric acid, to yield a first biphasic mixture including an aqueous layer and an organic layer, wherein, if the solvent miscible with both the organic solvent and water is acetone, the acetone is present in both the aqueous and organic layers;

(d) separating the aqueous and organic layers;

(e) optionally washing the organic layer with water, optionally washing the aqueous layer with the organic solvent or an additional organic solvent, and if washing either or both the aqueous and/or organic layers, combining the corresponding layers and washes, to yield (separately) a combined aqueous phase and a combined organic phase;

(f) optionally filtering the combined aqueous phase;

(g) adding, to the combined aqueous phase, an organic solvent which will form an azeotropic mixture with water to yield a second work-up mixture;

(h) distilling the second work-up mixture to azeotropically remove the water and organic solvents, to yield a first product residue:

(i) adding to the first product residue an alcoholic solvent and water, to yield a third work-up mixture;

(j) cooling the third work-up mixture to yield a benzhydrocodone hydrochloride as a precipitate; and (k) isolating the benzhydrocodone hydrochloride precipitate. In some embodiments, the alcoholic solvent is n-butanol (i.e., n-BuOH).

In some embodiments, the n-BuOH may dissolve a crude benzhydrocodone hydrochloride residue to a clear solution upon heating. In other embodiments, the reaction product may crystalize from the solution upon cooling.

In certain embodiments, the invention is directed to a method as described above, wherein the aqueous layer is washed with an organic solvent such as toluene, and the like; and wherein the organic layer is washed with water (Method A).

In certain embodiments, the invention is directed to a method as described above, wherein the organic layer is washed with water (and wherein the aqueous layer is not further washed with an organic solvent such as toluene, and the like) (Method B).

In one embodiment, the invention is directed to a process for the preparation of benzhydrocodone hydrochloride including the steps of (Method C):

(a) reacting hydrocodone free base with benzoic anhydride at a temperature in the range of from about 100° C. to about 200° C. to yield a reaction mixture including benzhydrocodone free base (and further including unreacted hydrocodone freebase and unreacted benzoic anhydride and benzoic acid):

(b) adding to the reaction mixture an organic solvent, a solvent which is miscible with both the organic solvent and water, and aqueous hydrochloric acid, to yield a first work-up mixture:

(c) adjusting the pH of the first work-up mixture to a pH in the range of from about pH 1.0 to about pH 5.0, wherein the pH is adjusted by addition of hydrochloric acid, to yield a first biphasic mixture including an aqueous layer and an organic layer, wherein, if the solvent miscible with both the organic solvent and water is acetone, then the acetone is present in both the aqueous and organic layers;

(d) separating the aqueous and organic layers:

(e) optionally washing the organic layer with water, optionally washing the aqueous layer with the organic solvent or an additional organic solvent, and if washing either or both the aqueous and/or organic layers, combining the corresponding layers and washes, to yield (separately) a combined aqueous phase and a combined organic phase:

(f) optionally filtering the combined aqueous phase;

(g) adjusting the pH of the combined aqueous phase to a pH in the range of from about pH 8.0 to about pH 11.0, to yield a second biphasic mixture including a second aqueous layer and a second organic layer;

(h) separating the second aqueous and second organic layers;

(i) optionally washing the second organic layer with water, optionally washing the second aqueous layer with the organic solvent or an additional organic solvent, and if washing either or both the aqueous and/or organic layers, combining the corresponding layers and washes, to yield (separately) a second combined aqueous phase and a second combined organic phase;

(j) adjusting the pH of the second combined organic layer (and wash(es)) with aqueous hydrochloric acid, to a pH in the range of from about pH 1.0 to about pH 5.0, to yield a fourth work-up mixture;

(k) removing the solvent from the fourth work-up mixture to yield a second product residue:

(l) adding to the second product residue an alcoholic solvent (preferably n-butanol) and water to yield a fifth work-up mixture:

(m) cooling the fifth work-up mixture to yield a benzhydrocodone hydrochloride as a precipitate; and (n) isolating the benzhydrocodone hydrochloride precipitate.

In some embodiments, the invention is directed to any process as described herein further including reacting thebaine, to yield hydrocodone free base, according to known methods. In a selected embodiment, the thebaine is CPS thebaine.

Thebaine is converted to hydrocodone free base in-situ, i.e., without isolating it from the reactor, and then reacted with benzoic anhydride at 100° C.-200° C. The resulting product mixture is then subjected to the previous work-up methods (A, B, or C) to complete the one-pot synthesis of benzhydrocodone hydrochloride.

In some embodiments, a compound having the crystal structure, i.e., Form 1, according to FIG. 1, may be prepared according to the methods disclosed herein.

In some embodiments, the invention is directed to process(es) for the preparation of benzhydrocodone hydrochloride wherein the benzhydrocodone hydrochloride product isolated has an improved impurity profile as compared to benzhydrocodone hydrochloride prepared according to other methods that may be known in the art.

In one embodiment, the invention is directed to a process for the crystallization or recrystallization of benzhydrocodone hydrochloride, as described in more detail hereinafter. In certain embodiments, the invention is directed to a process for the crystallization or recrystallization of benzhydrocodone including the steps of:

(a) admixing an alcoholic solvent, water, and a residue or reaction mixture including benzhydrocodone hydrochloride;

(b) cooling the mixture of step (a) to yield benzhydrocodone hydrochloride as a precipitate; and (c) optionally isolating the benzhydrocodone hydrochloride precipitate.

In one embodiment, the invention is directed to a process for the preparation of benzhydrocodone including the steps of:

(a) preparing a first mixture including benzoic anhydride, hydrocodone free base, and an organic solvent:

(b) removing a substantial portion of the organic solvent from the first mixture to afford a second mixture; and (c) heating the second mixture to a temperature in the range of about 100° C. to about 200° C.

In one embodiment, more than 90% of the organic solvent is removed. In one embodiment, more than 95% of the organic solvent is removed. In one embodiment, more than 99% of the organic solvent is removed. In one embodiment, the organic solvent is selected from the group consisting of toluene, ether, ethyl acetate, and THF. In one embodiment, the organic solvent is toluene, and wherein the toluene is removed from the reaction mixture by distillation. In one embodiment, the toluene is removed from the reaction mixture under a flow of $N_2$ gas.

In one embodiment, the invention is directed to a process for the preparation of benzhydrocodone hydrochloride including the steps of:

(a) mixing hydrocodone free base with benzoic anhydride and heating the mixture at a temperature in the range of from about 100° C. to about 200° C., to yield a mixture including benzhydrocodone free base;

(b) adding to the mixture a first organic solvent and a solvent which is miscible with both the first organic solvent and water;

(c) adding to the mixture an aqueous hydrochloric acid solution, and adjusting the pH of the mixture to a pH in the range of from about pH 1.0 to about pH 5.0, to yield a biphasic mixture:

(d) allowing the mixture to separate into an aqueous mixture layer and an organic mixture layer, and separating the aqueous mixture from the organic mixture;

(e) adding to the aqueous mixture a second organic solvent capable of dissolving benzoic anhydride and benzoic acid:

(f) heating the aqueous mixture to azeotropically remove by distillation a substantial portion of the water and the organic solvent to yield a product residue:

(g) adding to the product residue an alcoholic solvent and water, to yield a work-up mixture; and (h) cooling the work-up mixture to yield benzhydrocodone hydrochloride.

In one embodiment, the organic mixture layer of step (d) is further washed with water, resulting layers are separated, and the resulting aqueous layer is added to the aqueous mixture of step (d). In one embodiment, the aqueous mixture of step (d) is further washed with a third organic solvent, the resulting layers are separated, and the resulting organic layer is added to the organic mixture of step (d). In one embodiment, the third organic solvent is an aprotic solvent. In one embodiment, the aqueous mixture of step (d) is filtered. In one embodiment, benzhydrocodone hydrochloride is obtained as a precipitate. In one embodiment, benzhydrocodone hydrochloride is further isolated. In one embodiment, the first organic solvent is an aprotic solvent. In one embodiment, the second organic solvent is an aprotic solvent. In some embodiments, the aprotic solvent is toluene. In one embodiment, the solvent which is miscible with both the organic solvent and water is acetone. In one embodiment, the aqueous hydrochloric acid solution added in step (c) is 37% aqueous hydrochloric acid. In one embodiment, the pH of the mixture in step (c) is adjusted to pH 2.8. In one embodiment, the alcoholic solvent is n-butanol.

In one embodiment, the invention is directed to a pharmaceutical composition including a pharmaceutically acceptable carrier and benzhydrocodone prepared according to any process of the invention. In some embodiments, the invention is directed to a pharmaceutical composition including a pharmaceutically acceptable carrier and benzhydrocodone hydrochloride prepared according to any process of the invention. In one embodiment, the invention is directed to a product prepared according to any of the processes described herein.

Illustrative of the invention is a pharmaceutical composition including a pharmaceutically acceptable carrier and a product (e.g., benzhydrocodone hydrochloride or benzhydrocodone free base) prepared according to any of the processes described herein. An illustration of the invention is a pharmaceutical composition made by mixing product prepared according to any of the processes described herein and a pharmaceutically acceptable carrier. Illustrating the invention is a process for making a pharmaceutical composition including mixing a product prepared according to any of the processes described herein and a pharmaceutically acceptable carrier.

Exemplifying the invention are methods of treating pain including administering to a subject in need thereof a therapeutically effective amount of any of the compounds or pharmaceutical compositions described above.

In an embodiment, the invention is directed to a product prepared according to any of the processes described herein for use as a medicament. In another embodiment, the invention is directed to a product prepared according to any of the processes described herein for use in the treatment of pain. In another embodiment, the invention is directed to a composition including a product prepared according to any of the processes described herein for the treatment of pain.

Another example of the invention is the use of a benzhydrocodone product prepared according to any of the processes described herein in the preparation of a medicament for treating pain, in a subject in need thereof. In another example, the invention is directed to a product prepared according to any of the processes described herein for use in a methods for treating pain, in a subject in need thereof.

BRIEF DESCRIPTION OF THE DRAWINGS

The foregoing summary, as well as the following detailed description of embodiments of the invention, will be better understood when read in conjunction with the appended FIGURE.

FIG. 1 illustrates the X-ray diffraction pattern of benzhydrocodone Form 1 prepared according to the methods disclosed herein.

DETAILED DESCRIPTION OF THE INVENTION

The invention is directed to an improved process for the preparation of benzhydrocodone free base, wherein the improvement comprises improved handling and operability of the reaction, particularly under commercial or manufacturing conditions.

The invention is further directed to processes for the preparation of benzhydrocodone hydrochloride. In certain embodiments, the invention is directed to processes for the preparation of benzhydrocodone hydrochloride without isolation of benzhydrocodone free base, and yielding a product of improved yield and/or purity.

In certain embodiments, the invention is directed to processes for the preparation of benzhydrocodone, wherein the processes facilitate removal of starting materials and benzoic acid by-product from the isolated product, thereby improving product purity as compared to other methods that may be known in the art.

In certain embodiments, the invention is directed to processes for the preparation of benzhydrocodone hydrochloride, wherein the benzhydrocodone hydrochloride is prepared without isolation of the benzhydrocodone free base. In some embodiments, benzhydrocodone hydrochloride is prepared directly in the work-up. In other embodiments, isolation of the benzhydrocodone free base is typically achieved by basification of the reaction mixture. In certain embodiments, the invention is directed to processes for the preparation of benzhydrocodone hydrochloride wherein the solvent used in crystallizing the benzhydrocodone hydrochloride is selected to preferentially crystallize the desired product, i.e., benzhydrocodone hydrochloride, resulting in a product of improved purity, i.e., wherein the reaction starting materials and any by-products are highly soluble in the mother liquor and as such remain in solution during the crystallization. This crystallization enables the isolation of benzhydrocodone hydrocodone product that meets all active pharmaceutical ingredient (API) quality attributes via a single one-pot synthesis.

In certain embodiments, the invention is directed to processes for the preparation of benzhydrocodone hydrochloride from thebaine in a one-pot reaction, without isolation of hydrocodone freebase intermediate, thereby resulting in increasing overall product yield and/or purity.

Definitions

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the invention. In some embodiments, wherein the compound is present as an enantiomer, the enantiomer is present at an enantiomeric excess of greater than or equal to about 80%, at an enantiomeric excess of greater than or equal to about 90%, at an enantiomeric excess of greater than or equal to about 95%, at an enantiomeric excess of greater than or equal to about 98%, or at an enantiomeric excess of greater than or equal to about 99%. In one embodiment, the enantiomer is present at an enantiomeric excess of greater than or equal to about 81%. In another embodiment, the enantiomer is present at an enantiomeric excess of greater than or equal to about 82%. In another embodiment, the enantiomer is present at an enantiomeric excess of greater than or equal to about 83%. In another embodiment, the enantiomer is present at an enantiomeric excess of greater than or equal to about 84%. In another embodiment, the enantiomer is present at an enantiomeric excess of greater than or equal to about 85%. In another embodiment, the enantiomer is present at an enantiomeric excess of greater than or equal to about 86%. In another embodiment, the enantiomer is present at an enantiomeric excess of greater than or equal to about 87%. In another embodiment, the enantiomer is present at an enantiomeric excess of greater than or equal to about 88%. In another embodiment, the enantiomer is present at an enantiomeric excess of greater than or equal to about 89%. In another embodiment, the enantiomer is present at an enantiomeric excess of greater than or equal to about 91%. In another embodiment, the enantiomer is present at an enantiomeric excess of greater than or equal to about 92%. In another embodiment, the enantiomer is present at an enantiomeric excess of greater than or equal to about 93%. In another embodiment, the enantiomer is present at an enantiomeric excess of greater than or equal to about 94%. In another embodiment, the enantiomer is present at an enantiomeric excess of greater than or equal to about 96%. In another embodiment, the enantiomer is present at an enantiomeric excess of greater than or equal to about 97%.

Similarly, wherein the compound is present as a diastereomer, the diastereomer is present at a diastereomeric excess of greater than or equal to about 80%, at a diastereomeric excess of greater than or equal to about 90%, at a diastereomeric excess of greater than or equal to about 95%, at a diastereomeric excess of greater than or equal to about 98%, or at a diastereomeric excess of greater than or equal to about 99%. In one embodiment, the diastereomer is present at a diastereomeric excess of greater than or equal to about 81%. In another embodiment, the diastereomer is present at a diastereomeric excess of greater than or equal to about 82%. In another embodiment, the diastereomer is present at a diastereomeric excess of greater than or equal to about 83%. In another embodiment, the diastereomer is present at a diastereomeric excess of greater than or equal to about 84%. In another embodiment, the diastereomer is present at a diastereomeric excess of greater than or equal to about 85%. In another embodiment, the diastereomer is present at a diastereomeric excess of greater than or equal to about 86%. In another embodiment, the diastereomer is present at a diastereomeric excess of greater than or equal to about 87%. In another embodiment, the diastereomer is present at a diastereomeric excess of greater than or equal to about 88%. In another embodiment, the diastereomer is present at a diastereomeric excess of greater than or equal to about 89%. In another embodiment, the diastereomer is present at a diastereomeric excess of greater than or equal to about 91%. In another embodiment, the diastereomer is present at a diastereomeric excess of greater than or equal to about 92%. In another embodiment, the diastereomer is present at a diastereomeric excess of greater than or equal to about 93%. In another embodiment, the diastereomer is present at a diastereomeric excess of greater than or equal to about 94%. In another embodiment, the diastereomer is present at a diastereomeric excess of greater than or equal to about 96%. In another embodiment, the diastereomer is present at a diastereomeric excess of greater than or equal to about 97%.

Furthermore, some of the crystalline forms for the compounds of the invention may exist as polymorphs and as such are intended to be included in the invention. In addition, some of the compounds of the invention may form solvates with water, i.e., hydrates, or common organic solvents, and such solvates are also intended to be encompassed within the scope of this invention.

Furthermore, it is intended that within the scope of the invention, any element, in particular when mentioned in relation to benzhydrocodone compounds described herein (e.g., benzhydrocodone or benzhydrocodone hydrochloride), shall comprise all isotopes and isotopic mixtures of said element, either naturally occurring or synthetically produced, either with natural abundance or in an isotopically enriched form. For example, a reference to hydrogen includes within its scope $^{1}H$, $^{2}H$ (D), and $^{3}H$ (T). Similarly, references to carbon and oxygen include within their scope respectively $^{11}C$, $^{12}C$, $^{13}C$, and $^{14}C$, and $^{16}O$ and $^{18}O$. The isotopes may be radioactive or non-radioactive. Radiolabelled isomers of the compounds and/or products described herein (e.g., benzhydrocodone or benzhydrocodone hydrochloride) may comprise a radioactive isotope selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$, and $^{18}F$.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

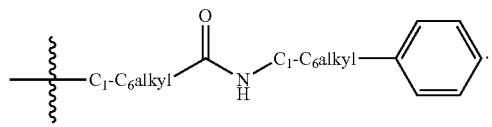

Abbreviations used in the specification, particularly the Schemes and Examples, are as follows:

| | |
|---|---|
| Ar = | Aryl group |
| AcOH = | Acetic acid |
| BSA = | Bovine Serum Albumin |
| DCE = | Dichloroethane |
| DEA = | Diethylamine |
| DEAD = | Diethylazodicarboxylate |
| DIAD = | Diisopropylazodicarboxylate |
| DIPEA or DIEA = | Diisopropylethylamine |
| DMAP = | 4-N,N-Dimethylaminopyridine |
| DMF = | N,N-Dimethylformamide |
| DMSO = | Dimethylsulfoxide |
| $D_2O$ = | Deuterated water |
| EDTA = | Ethylene Diamine Tetraacetic Acid |
| $Et_3N$ = | Triethylamine |
| $Et_2O$ = | Diethyl ether |
| EtOAc = | Ethyl acetate |
| EtOH = | Ethanol |
| HATU = | O-(7-Azabenzotriazol-1-yl)-N,N,N",N"-Tetramethyl Uronium Hexafluorophosphate |
| HEPES = | 4-(2-Hydroxyethyl)-1-Piperizine Ethane Sulfonic Acid |
| HOBT = | 1-Hydroxybenzotriazole |
| HPLC = | High Pressure Liquid Chromatography |
| MeOH = | Methanol |
| Mesyl = | Methylsulfonyl |
| $Na(OAc)_3BH$ = | Sodium triacetoxyborohydride |
| NaOEt = | Sodium Ethoxide |
| NMP = | N-methyl-2-pyrrolidinone |
| PBS = | Phosphate Buffered Saline |
| Pd—C = | Palladium on Carbon Catalyst |
| $Pd_2(OAc)_2$ = | Palladium(II)acetate |
| $Pd_2(dba)_3$ = | Tris(dibenzylidene acetone)dipalladium(0) |
| $Pd(PPh_3)_4$ = | Tetrakistriphenylphosphine palladium (0) |
| $Pd(PPh_3)_2Cl_2$ = | Bis(triphenylphosphine)palladium (II) chloride |
| Ph = | Phenyl |
| RT or rt = | Room temperature |
| t-BOC or Boc = | Tert-Butoxycarbonyl |
| TEA = | Triethylamine |
| TFA = | Trifluoroacetic Acid |
| THF = | Tetrahydrofuran |
| TLC = | Thin Layer Chromatography |
| TMOF = | Trimethylorthoformate |
| Tosyl = | p-Toluenesulfonyl |
| Tris HCl or Tris-Cl = | Tris[hydroxymethyl]aminomethyl hydrochloride |

As used herein, unless otherwise noted, the term "isolated form" shall mean that the compound is present in a form which is separate from any solid mixture with another compound(s), solvent system or biological environment. In an embodiment of the invention, the benzhydrocodone hydrochloride is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the invention, the benzhydrocodone hydrochloride is present as a substantially pure form.

As used herein, unless otherwise noted, the terms "treating". "treatment," and the like, shall include the management and care of a subject or patient, for the purpose of combating a disease, condition, or disorder and includes the administration of a compound of the invention to prevent the onset of the symptoms or complications, alleviate the symptoms or complications, or eliminate the disease, condition, or disorder. In one embodiment, the subject or patient is preferably a mammal. In another embodiment, the subject or patient is more preferably human.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the invention is directed to methods of prevention, a subject in need of thereof. i.e., a subject in need of prevention, shall include any subject or patient, preferably a mammal, and more preferably a human, who has experienced or exhibited at least one symptom of the disorder, disease, or condition to be prevented. Further, a subject in need thereof may additionally be a subject, preferably a mammal, and more preferably a human, who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease, or condition, and therefore in need of prevention or preventive treatment as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation, or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g., base, solvent, etc.) is recited in more than one step of a process, the individual reagents are independently selected for each reaction step and may be the same or different from each other. For example, wherein two steps of a process recite an organic or inorganic base as a reagent, the organic or inorganic base selected for the first step may be the same or different than the organic or inorganic base of the second step. Further, one skilled in the art will recognize that wherein a reaction step of the invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product, i.e., the product of the first of the two consecutive reaction or process steps, then the first and second reaction or process steps may be run in the same solvent or solvent system; or alternatively may be run in different solvents or solvent systems following solvent exchange, which may be completed according to known methods.

One skilled in the art will further recognize that the reaction or process step(s) as herein described or claimed are allowed to proceed for a sufficient period of time until the reaction is complete, as determined by any method known to one skilled in the art, for example, chromatography (e.g., HPLC). In this context a "completed reaction or process step" shall mean that the reaction mixture contains a significantly diminished amount of the starting material(s) and/or reagent(s), and a significantly increased amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

During any of the processes for preparation of the compounds of the invention, it may be necessary and/or desirable to protect sensitive or reactive groups on any of the molecules concerned. This may be achieved by means of conventional protecting groups, such as those described in Protective Groups in Organic Chemistry, ed. J.F.W. McOmie, Plenum Press, 1973; and T.W. Greene & P.G.M. Wuts, Protective Groups in Organic Synthesis, John Wiley & Sons, 1991, the entirety of which are incorporated herein by reference. The protecting groups may be removed at a convenient subsequent stage using methods known from the art.

One skilled in the art will recognize that wherein a reaction step of the invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows:

$$[(R\text{moles}-S\text{moles})/(R\text{moles}+S\text{moles})]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-}\max])\times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Methods and Processes for the Preparation of Benzhydrocodone and Benzhydrocodone Hydrochloride In an embodiment, the invention is directed to methods and processes for the preparation of benzhydrocodone hydrochloride. In an embodiment, benzhydrocodone hydrochloride is prepared from hydrocodone free base as described in more detail in Scheme 1, below (Methods A & B).

Scheme 1

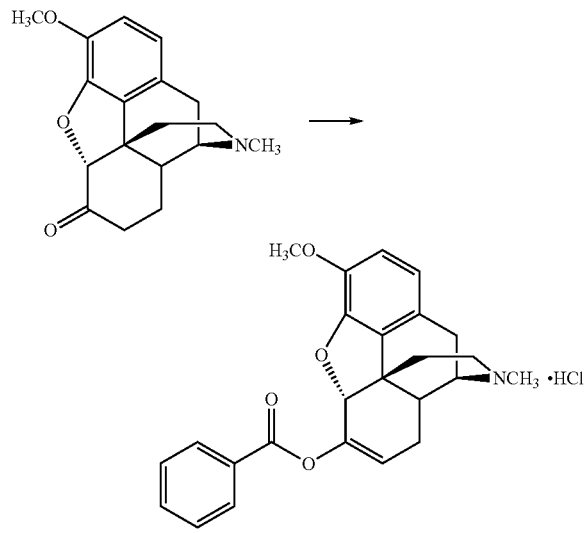

Accordingly, hydrocodone free base is reacted with benzoic anhydride at a temperature in the range of from about 100° C. to about 200° C., preferably at a temperature in the range of from about 120° C. to about 150° C., to yield a reaction mixture including benzhydrocodone free base, and further including one or more of unreacted hydrocodone free base, unreacted benzoic anhydride, and/or benzoic acid as a by-product.

Preferably, benzoic anhydride is added to the hydrocodone free base as a mixture with a suitably selected organic solvent such as toluene, ethyl acetate, THF, ether, and the like, and wherein, the resulting mixture including hydrocodone free base, benzoic acid and the organic solvent is heated, preferably under a nitrogen stream, to distill (remove) the organic solvent.

In one embodiment, the resulting mixture is a reaction mixture. In an embodiment, the organic solvent is toluene.

To the reaction mixture including benzhydrocodone are added:

(a) a suitably selected organic solvent, preferably an organic solvent which will dissolve benzoic anhydride and benzoic acid, such as TBME, ethyl ether, toluene, and the like, preferably toluene, wherein the organic solvent is present in an amount in the range of from about 2 ml per each gram of hydrocodone to about 3 ml per each gram of hydrocodone, preferably in an amount in the range of from about 2.2 ml per each gram of hydrocodone to about 2.6 ml per each gram of hydrocodone, more preferably in an amount of about 2.6 ml per each gram of hydrocodone; and (b) a solvent which is miscible with both the organic solvent and water such as acetone, THF, methanol, ethanol, and the like (but preferably THF or acetone; or more preferably acetone), wherein the solvent is present in an amount in the range of from about 3 ml per each gram of hydrocodone to about 6 ml per each gram of hydrocodone, preferably in an amount in the range of from about 4 ml per each gram of hydrocodone to about 5 ml per each gram of hydrocodone, more preferably in an amount of about 5 ml per each gram of hydrocodone; to yield a first work-up mixture including benzhydrocodone hydrochloride.

The pH of the first work-up or product mixture is adjusted with hydrochloric acid, preferably aqueous hydrochloric acid solution, more preferably 37% aqueous hydrochloric acid, to a pH in the range of from about pH 1.0 to about pH 5.0, preferably to a pH in the range of from about pH 2 to pH 4, more preferably to a pH in the range of from about pH 2.5 to about pH 3; to yield a first biphasic mixture including an aqueous layer and an organic layer, wherein, when the organic solvent which is miscible in both the organic solvent and water is acetone, the acetone is present in both the aqueous and organic layers.

One skilled in the art will recognize that the benzhydrocodone hydrochloride will be present in the aqueous layer, whereas unreacted hydrocodone free base (e.g., about 1%), unreacted benzoic anhydride, and side products will be present in the organic layer.

The aqueous and organic layers are separated. The organic layer is optionally washed one or more times with water (to further extract any benzhydrocodone hydrochloride which may be present in the organic layer). If the organic layer is washed with water, then the aqueous layer and aqueous washes are combined. The combined aqueous layer (and wash(es)) are then optionally filtered according to known methods, to remove any solid particulates.

The aqueous layer is optionally washed with a suitably selected organic solvent, preferably toluene. If the aqueous layer is washed with the organic solvent, the organic layer and organic solvent wash(es) are optionally combined.

To the combined aqueous layer (and wash(es)) is added a second suitably selected organic solvent, preferably an organic solvent which will form an azeotropical mixture with water, wherein the second organic solvent is present in an amount in the range of from about 3 ml per each gram of hydrocodone to about 12 ml per each gram of hydrocodone, preferably in an amount in the range of from about 4 ml per each gram of hydrocodone to about 10 ml per each gram of hydrocodone, more preferably in an amount of about 10 ml per each gram of hydrocodone; to yield a second work-up mixture.

The second work-up mixture is heated to azeotropically distill the water and organic solvent, to yield a first product residue.

To the first product residue are added an alcoholic solvent such as n-butanol, isopropyl alcohol (IPA), ethanol (EtOH), methanol (MeOH), and the like, preferably n-butanol, and water, wherein the alcoholic organic solvent is present in an amount in the range of from about 1 ml per each gram of hydrocodone to about 5 ml per each gram of hydrocodone, preferably in an amount in the range of from about 2 ml per each gram of hydrocodone to about 4 ml per each gram of hydrocodone, more preferably in an amount of about 3.36 ml per each gram of hydrocodone; and wherein the water is present in an amount in the range of from about 0.02 ml per each gram of hydrocodone to about 0.08 ml per each gram of hydrocodone, preferably an amount in the range of from about 0.05 ml per each gram of hydrocodone to about 0.1 ml per each gram of hydrocodone, more preferably in an amount of about 0.08 ml per each gram of hydrocodone; to yield a third work-up mixture; which third work-up mixture is heated up to dissolution and then cooled, preferably to a temperature in the range of from about 0° C. to about 15° C., more preferably to a temperature in the range of from about 2° C. to about 5° C. to yield benzhydrocodone hydrochloride as a precipitate. The benzhydrocodone hydrochloride precipitate is preferably isolated as a solid according to known methods, for example by filtration.

The invention is directed to a process for the preparation of benzhydrocodone hydrochloride from hydrocodone free base as described in more detail in Scheme 2, below (Method C).

Scheme 2

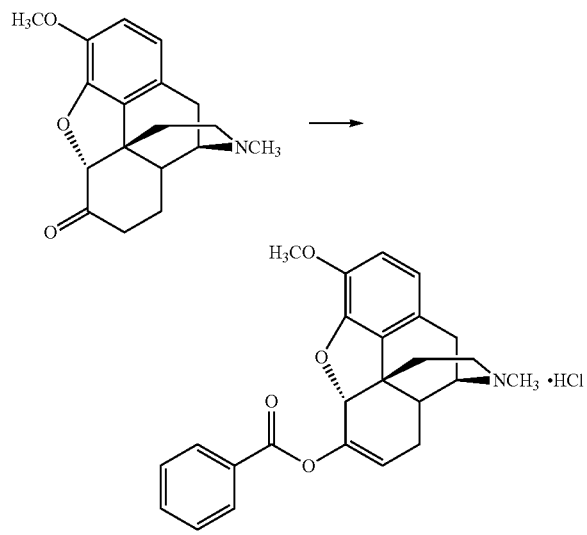

Accordingly, hydrocodone free base is reacted with benzoic anhydride; at a temperature in the range of from about 100° C. to about 200° C., preferably at a temperature in the range of from about 120° C. to about 150° C.; to yield a reaction mixture including benzhydrocodone free base, and further including one or more of unreacted hydrocodone free base, unreacted benzoic anhydride and/or benzoic acid as a by-product.

Preferably, benzoic anhydride is added to the hydrocodone free base as a mixture with a suitably selected organic solvent such as toluene, ethyl acetate, THF, ether, and the like (but preferably toluene); and the resulting reaction mixture (including hydrocodone free base, benzoic acid and the organic solvent) is heated, preferably under an nitrogen stream, to distill (remove) the organic solvent.

To the reaction mixture including benzhydrocodone are added:

(a) a suitably selected organic solvent, preferably an organic solvent which will dissolve benzoic anhydride and benzoic acid, such as TBME, ethyl ether, toluene, and the like, preferably toluene, wherein the organic solvent is present in an amount in the range of from about 2 ml per each gram of hydrocodone to about 3 ml per each gram of hydrocodone, preferably in an amount in the range of from about 2.2 ml per each gram of hydrocodone to about 2.6 ml per each gram of hydrocodone, more preferably in an amount of about 2.6 ml per each gram of hydrocodone; and (b) a solvent which is miscible with both the organic solvent and water such as acetone, THF, methanol, ethanol, and the like, preferably THF or acetone, and more preferably acetone, wherein the solvent is present in an amount in the range of from about 3 ml per each gram of hydrocodone to about 6 ml per each gram of hydrocodone, preferably in an amount in the range of from about 4 ml per each gram of hydrocodone to about 5 ml per each gram of hydrocodone, more preferably in an amount of about 5 ml per each gram of hydrocodone; to yield a first work-up mixture including benzhydrocodone hydrochloride.

The pH of the first product mixture is adjusted with hydrochloric acid, preferably aqueous hydrochloric acid, more preferably 37% aqueous hydrochloric acid, to a pH in the range of from about pH 1.0 to about pH 5.0, preferably to a pH in the range of from about pH 2 to pH 4, more preferably to a pH in the range of from about pH 2.5 to about pH 3, to yield a first biphasic mixture including an aqueous layer and an organic layer, and wherein, when the solvent that is miscible in both the organic solvent and water is acetone, the acetone is present in both the aqueous and organic layers.

One skilled in the art will recognize that the benzhydrocodone hydrochloride will be present in the aqueous layer, whereas unreacted hydrocodone free base (e.g., about 1%) and/or unreacted benzoic anhydride will be present in the organic layer.

In one embodiment, the aqueous and organic layers are separated. The organic layer is optionally washed one or more times with water, to further extract any benzhydrocodone hydrochloride which may be present in the organic layer. In one embodiment, the organic layer is washed with water, and then the aqueous layer and aqueous washes are combined. The combined aqueous layer (and wash(es)) are then optionally filtered according to known methods, to remove any solid particulates.

The aqueous layer is optionally washed with a suitably selected organic solvent, preferably the organic solvent added to the reaction mixture. In certain embodiments, the suitably selected organic solvent is toluene. In one embodiment, the aqueous layer is washed with the organic solvent, and the organic layer and organic solvent wash(es) are optionally combined.

The pH of the combined aqueous layer (and wash(es)) is adjusted to a pH in the range of from about pH 8 to about pH 11, preferably to a pH in the range of from about pH 8 to about pH 9, more preferably to a pH of about 8.5-9; wherein the pH is adjusted with a suitably selected base such as NH$_4$OH, NaOH, and the like, preferably NH$_4$OH; and a suitably selected third organic solvent such as toluene, ethyl acetate, ether, and the like, preferably toluene, is added, wherein the third organic solvent is added in an amount in the range of from about 1 ml per each gram of hydrocodone to about 10 ml per each gram of hydrocodone, preferably in an amount in the range of from about 2 ml per each gram of hydrocodone to about 4 ml per each gram of hydrocodone, more preferably in an amount of about 2.5 ml per each gram of hydrocodone, to yield a second biphasic mixture, including a second aqueous layer and a second organic layer.

One skilled in the art will recognize that upon basification of the combined aqueous layer, and wash(es), benzhydrocodone hydrochloride is converted to the corresponding benzhydrocodone free base, which moves from the aqueous to the organic phase, thereby allowing for removal of the aqueous phase without need of distillation as described with reference to Scheme 1, above.

In one embodiment, the second aqueous and second organic layers are separated. The second aqueous layer is optionally washed to further extract any benzhydrocodone free base which may be present in the second aqueous layer with a suitably selected organic solvent, preferably the third organic solvent, and more preferably toluene. In one embodiment, the second aqueous layer is washed with the organic solvent, and the organic layer and organic solvent wash(es) are combined. The second combined organic layer (and wash(es)) are then optionally filtered according to known methods, to remove any solid particulates.

The second organic layer is optionally washed one or more times with water. In one embodiment, the second organic layer is washed with water, and then the second aqueous layer and aqueous washes are combined.

To the combined second organic phase, and optional wash(es), is added water in the range of from about 1 ml per each gram of hydrocodone to about 1.5 ml per each gram of hydrocodone, preferably in an amount of about 1.2 ml per each gram of hydrocodone. One skilled in the art will recognize that the water is added to ease the pH adjustment.

The pH of the combined second organic phase, and optional wash(es), is adjusted with hydrochloric acid, preferably aqueous hydrochloric acid, more preferably 37% aqueous hydrochloric acid, to a pH in the range of from about pH 1.0 to about pH 5.0, preferably to a pH in the range of from about pH 2 to pH 4, more preferably to a pH in the range of from about pH 2.5 to about pH 3.

In one embodiment, the fourth work-up mixture is heated to effect a solvent swap, wherein the fourth work-up mixture is heated to remove the toluene and water, preferably to a temperature in the range of from about 70° C. to about 130° C., more preferably to a temperature in the range of from about 100° C. to about 120° C., to yield a first product residue.

In some embodiments, to the first product residue are added:

(a) an alcoholic solvent such as n-butanol, isopropyl alcohol (IPA), ethanol (EtOH), methanol (MeOH), and the like, preferably n-butanol, wherein the alcoholic solvent is present in an amount in the range of from about 1 ml per each gram of hydrocodone to about 5 ml per each gram of hydrocodone, preferably in an amount in the range of from about 2 ml per each gram of hydrocodone to about 4 ml per each gram of hydrocodone, more preferably in an amount of about 3.36 ml per each gram of hydrocodone; and (b) water; wherein the water is present in an amount in the range of from about 0.02 ml per each gram of hydrocodone to about 0.08 ml per each gram of hydrocodone, preferably an amount in the range of from about 0.05 ml per each gram of hydrocodone to about 0.1 ml per each gram of hydrocodone, more preferably in an amount of about 0.08 ml per each gram of hydrocodone; to yield a third work-up mixture.

In one embodiment, the third work-up mixture is heated to effect dissolution; and then cooled to effect precipitation of the desired benzhydrocodone hydrochloride, preferably to a temperature in the range of from about 0° C. to about 15° C., more preferably to a temperature in the range of from about 2° C. to about 5° C. to yield benzhydrocodone hydrochloride as a precipitate. In one embodiment, the benzhydrocodone hydrochloride precipitate is preferably isolated as a solid according to known methods, for example, by filtration.

One skilled in the art will recognize that the water added to the n-butanol/benzhydrocodone hydrochloride mixture is added to ensure an effective crystallization and the crystallization of the preferred hydrate form.

In an embodiment, the invention is directed to a one-pot process for the preparation of benzhydrocodone hydrochloride from thebaine, as described in more detail in Scheme 3, below.

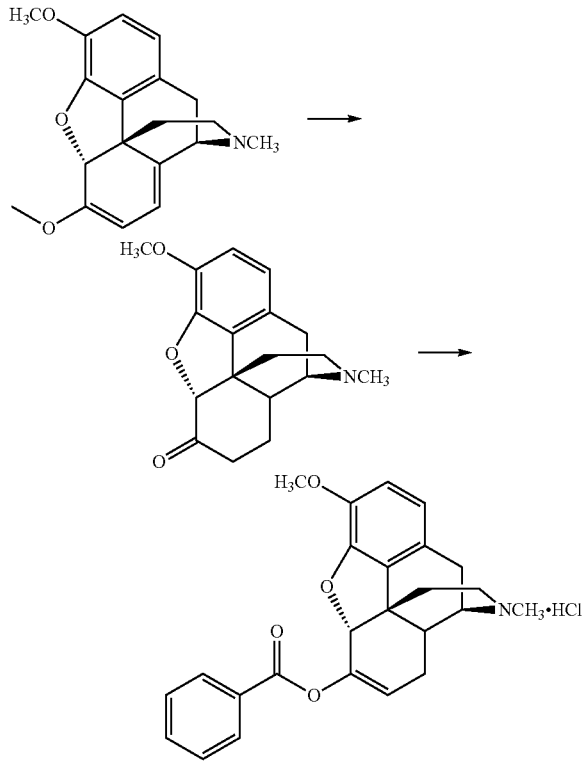

Scheme 3

Accordingly, CPS thebaine is reduced by reacting with a suitably selected reducing agent such as p-TSH (p-Toluene-sulfonyl hydrazide), and the like, in a suitably selected organic solvent, followed by acid hydrolysis in a suitably selected solvent, to yield hydrocodone free base, which is preferably not isolated.

The resulting hydrocodone free base is reacted with benzoic anhydride at about 100° C. to about 200° C., as described above; and further processed according to any of work-up Methods A, B. or C, as described in Schemes 1 and 2, above, to yield benzhydrocodone hydrochloride.

In another aspect, the invention is further directed to a process for the crystallization or recrystallization of benzhydrocodone hydrochloride, including:
(a) admixing
  (i) an alcoholic solvent such as methanol (MeOH), ethanol (EtOH), isopropyl alcohol (IPA), n-butanol, and the like, preferably n-butanol;
  (ii) water; and
  (iii) a residue or reaction mixture including benzhydrocodone hydrochloride, to yield a crystallization mixture:
(b) heating the crystallization mixture of step (a) to effect dissolution and to yield a solution;
(c) cooling the solution of step (b) to yield benzhydrocodone hydrochloride as a precipitate; and
(d) optionally isolating the benzhydrocodone hydrochloride precipitate.

Pharmaceutical Compositions

The invention further comprises pharmaceutical compositions containing a therapeutically effective amount of a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs, and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000) mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably, these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the invention. In one embodiment, the solid preformulation composition is subdivided into unit dosage forms containing from about 0.01 mg to about 0.1 mg. In another embodiment, the solid preformulation composition is subdivided into unit dosage forms containing from about 0.05 mg to about 0.5 mg. In another embodiment, the solid preformulation composition is subdivided into unit dosage forms containing from about 0.1 mg to about 1 mg. In another embodiment, the solid preformulation composition is subdivided into unit dosage forms containing from about 0.5 mg to about 5 mg. In another embodiment, the solid preformulation composition is subdivided into unit dosage forms containing from about 1 mg to about 10 mg. In another embodiment, the solid preformulation composition is subdivided into unit dosage forms containing from about 5 mg to about 50 mg. In another embodiment, the solid preformulation composition is subdivided into unit dosage forms containing from about 10 mg to about 100 mg. In another embodiment, the solid preformulation composition is subdivided into unit dosage forms containing from about 50 mg to about 500 mg. In another embodiment, the solid preformulation composition is subdivided into unit dosage forms containing from about 250 mg to about 750 mg. In another embodiment, the solid preformulation composition is subdivided into unit dosage forms containing from about 500 mg to about 1000 mg.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating pain and other disorders described in the invention may also be carried out using a pharmaceutical composition including a therapeutically effective amount of any of the compounds as defined herein and a pharmaceutically acceptable carrier. The pharmaceutical composition may contain between about 0.01 mg and about 1000 mg of the compound, or any amount or range therein, preferably from about 1.0 mg to about 500 mg of the compound, or any amount or range therein, and may be constituted into any form suitable for the mode of administration selected. In one embodiment, the pharmaceutical composition contains between about 0.01 mg and about 1 mg of the compound. In another embodiment, the pharmaceutical composition contains between about 0.05 mg and about 5 mg of the compound. In another embodiment, the pharmaceutical composition contains between about 2.5 mg and about 10 mg of the compound. In another embodiment, the pharmaceutical composition contains between about 5 mg and about 25 mg of the compound. In another embodiment, the pharmaceutical composition contains between about 15 mg and about 50 mg of the compound. In another embodiment, the pharmaceutical composition contains between about 25 mg and about 75 mg of the compound. In another embodiment, the pharmaceutical composition contains between about 50 mg and about 100 mg of the compound. In another embodiment, the pharmaceutical composition contains between about 75 mg and about 250 mg of the compound. In another embodiment, the pharmaceutical composition contains between about 125 mg and about 500 mg of the compound. In another embodiment, the pharmaceutical composition contains between about 300 mg and about 750 mg of the compound. In another embodiment, the pharmaceutical composition contains between about 650 mg and about 1000 mg of the compound.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the invention may be administered in a single daily dose, or the total daily dosage may be administered in divided doses of two, three or four times daily. Furthermore, compounds for the invention can be administered in intranasal form via topical use of suitable intranasal vehicles, or via transdermal skin patches well known to those of ordinary skill in that art. To be administered in the form of a transdermal delivery system, the dosage administration will be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms include, in some embodiments, any suitably flavored suspending or dispersing agents such as synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the invention, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain, the entirety of which is incorporated herein by reference.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the entirety of which are incorporated herein by reference.

Dosage

Compounds of this invention may be administered in any of the foregoing compositions and according to dosage regimens established in the art whenever treatment of pain is required.

The daily dosage of the products may be varied over a wide range, from about 0.01 mg to about 1,000 mg per adult human per day, or any amount or range therein. In one embodiment, the daily dosage of the products may be from about 0.01 mg to about 5 mg per adult human per day. In another embodiment, the daily dosage of the products may be from about 2.5 mg to about 10 mg per adult human per day. In another embodiment, the daily dosage of the products may be from about 5 mg to about 25 mg per adult human per day. In another embodiment, the daily dosage of the products may be from about 15 mg to about 50 mg per adult human per day. In another embodiment, the daily dosage of the products may be from about 25 mg to about 75 mg per adult human per day. In another embodiment, the daily dosage of the products may be from about 50 mg to about 100 mg per adult human per day. In another embodiment, the daily dosage of the products may be from about 75 mg to about 250 mg per adult human per day. In another embodiment, the daily dosage of the products may be from about 125 mg to about 500 mg per adult human per day. In another embodiment, the daily dosage of the products may be from about 350 mg to about 750 mg per adult human per day. In another embodiment, the daily dosage of the products may be from about 500 mg to about 1000 mg per adult human per day.

For oral administration, the compositions are preferably provided in the form of tablets containing, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 100 mg, about 150 mg, about 200 mg, about 250 mg, and/or about 500 mg of the active ingredient for the symptomatic adjustment of the dosage to the patient to be treated. An effective amount of the drug is ordinarily supplied at a dosage level of from about 0.01 mg % kg to about 500 mg/kg of body weight per day, or any amount or range therein. Preferably, the range is from about 0.1 to about 50.0 mg/kg of body weight per day, or any amount or range therein. More preferably, from about 0.5 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known, and generally accepted cell and/or animal models are predictive of the ability of a test compound to treat or prevent a given disorder.

One skilled in the art will further recognize that human clinical trials, including first-in-human, dose ranging, and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Examples 1 through 4 describe recipes and/or procedures for the synthesis of the title compounds. Several batches of said compounds were prepared according to the recipes and/or procedures as described below. The physical properties (e.g., MS+, 1H NMR, etc.) listed at the end of the synthesis descriptions below are a listing of the physical properties measured for a representative sample of the prepared compound.

Example 1

One-Step Synthesis of Benzhydrocodone Hydrochloride from Hydrocodone Base—Method A

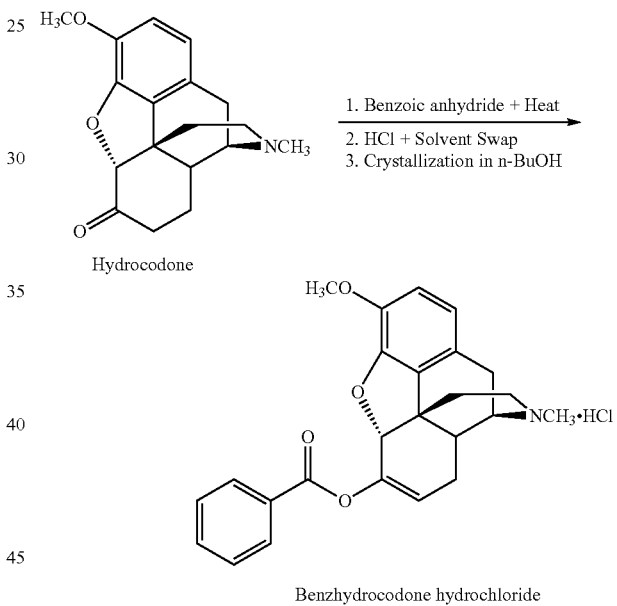

Hydrocodone base (50.0 g, 0.17 mol), benzoic anhydride (125.1 g, 0.553 mol), and toluene (100 mL), were charged to a 1 L 3-necked flask. The resulting mixture was heated to 100° C.-130° C. to distill off toluene under a $N_2$ sweep. The reaction mixture temperature was held at 130° C. for an additional 10 hrs. The reaction mixture was cooled to ambient temperature and then quenched by the addition of toluene (130 mL), acetone (250 mL), and an acid solution made by mixing HCl (37%, 7.75 g) in water (250 mL). The pH was adjusted to 2.8-3.0 with additional 37% HCl as needed. The mixture was allowed to settle for phase separation. The upper toluene/benzoic anhydride layer was washed with water (150 mL). The two aqueous/product layers were combined and washed with toluene (150 mL×2). The upper toluene/acetone layer was discarded. The bottom aqueous/product layer was filtered to remove any insoluble matter. To the filtrate was added toluene (500 mL) and the resulting mixture was heated to 80° C.-110° C. to azeotropically distill off water/toluene using a Dean-Stark apparatus. When the removal of water was complete, the remaining toluene was swapped out with n-butanol (168 mL). To the reaction mixture was added water (4 g) and the resulting slurry was heated to reflux to achieve a clear solution. The reaction mixture was then cooled, filtered, washed with toluene, and dried to yield benzhydrocodone hydrochloride as a white crystalline solid (56.94 g, 78%); Chromatographic Purity: Benzhydrocodone 99.9%, Hydrocodone 0.07%, Total Other Impurities 0.05%.

Example 2

One-Step Synthesis of Benzhydrocodone Hydrochloride from Hydrocodone Base—Method B

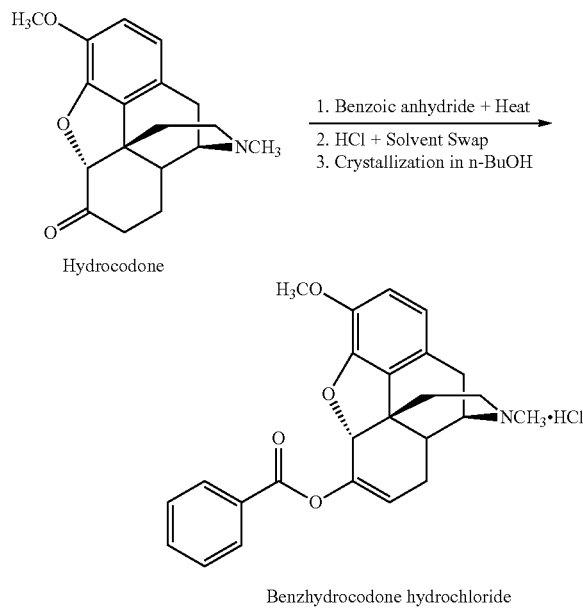

Hydrocodone

Benzhydrocodone hydrochloride

Hydrocodone base (50.0 g, 0.17 mol), benzoic anhydride (125.1 g, 0.553 mol), and toluene (100 mL), were charged to a IL 3-necked flask. The resulting mixture was heated to 100° C.-130° C. to distill off toluene under a N₂ sweep. The reaction mixture temperature was held at 130° C. for an additional 10 hrs. The reaction mixture was cooled to ambient temperature and then quenched by the addition of toluene (130 mL), acetone (250 mL), and an acid solution made by mixing HCl (37%, 7.75 g) in water (250 mL). The pH was adjusted to 2.8-3.0 with additional 37% HCl as needed. The mixture was allowed to settle for phase separation. The upper toluene/benzoic anhydride layer was washed with water (150 mL). The upper toluene/acetone layer was discarded. The bottom aqueous/product layers were combined and filtered to remove any insoluble matter. To the filtrate was added toluene (500 mL) and the resulting mixture was heated to 80° C.-110° C. to azeotropically distill off water/toluene using a Dean-Stark apparatus. When the removal of water was complete, the remaining toluene was swapped out with n-butanol (168 mL). To the reaction mixture was added water (4 g) and the resulting slurry was heated to reflux to achieve a clear solution. The reaction mixture was then cooled, filtered, washed with toluene and dried to yield benzhydrocodone hydrochloride as white crystalline solids (61.82 g, 84%). Chromatographic Purity: Benzhydrocodone 99.8%, Hydrocodone 0.10%, Total Other Impurities 0.06%.

Example 3

One-Step Synthesis of Benzhydrocodone Hydrochloride from Hydrocodone Base, Method C

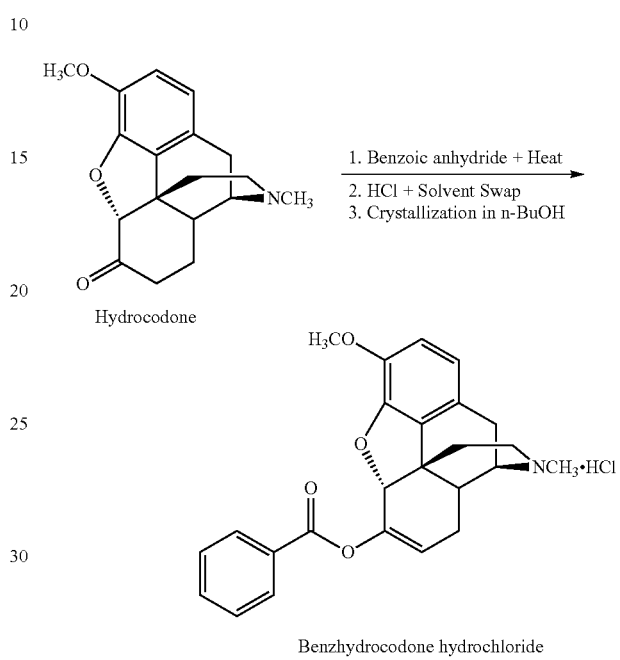

Hydrocodone

Benzhydrocodone hydrochloride

Hydrocodone base (25.0 g, 0.08 mol), benzoic anhydride (62.5 g, 0.28 mol), and toluene (50 mL), were charged to a 500 mL 3-necked flask. The resulting mixture was heated to 100° C.-130° C. to distill off toluene under a N₂ sweep. The reaction mixture temperature was held at 130° C. for an additional 10 hrs. The reaction mixture was cooled to ambient temperature and then quenched by the addition of toluene (65 mL), acetone (125 mL), and an acid solution made by mixing HCl (37%, 3.88 g) in water (125 mL). The pH was adjusted to 2.8-3.0 with additional 37% HCl as needed. The mixture was allowed to settle for phase separation. The upper toluene/benzoic anhydride layer was washed with water (75 mL). The upper toluene/acetone layer was discarded. The bottom aqueous/product layers were combined and filtered to remove any insoluble matter.

The pH of filtrate was adjusted to 8.5-9.00 using ammonia hydroxide (28%, 11.42 g). Toluene (65 mL) was then added to the reaction mixture for product extraction and phase separation. The bottom aqueous layer was extracted again with additional toluene (100 mL). The two upper toluene/product layers were combined, and a small of amount of water (30 mL) was added to it. The pH of the reaction mixture was adjusted to 2.80 using HCl (37%/0, as needed). The reaction mixture was heated up to swap the solvents (toluene+water) out with n-butanol (84 mL). To the reaction mixture was added water (2 g) and the resulting slurry was heated to reflux to achieve a clear solution. The reaction mixture was then cooled, filtered, washed with toluene and dried to yield benzhydrocodone hydrochloride as white crystalline solids (26.83 g, 73%); Chromatographic Purity: Benzhydrocodone 99.9/%, Hydrocodone 0.05%, Total Other Impurities 0.07%.

Example 4

One-Step Synthesis of Benzhydrocodone Hydrochloride from Thebaine

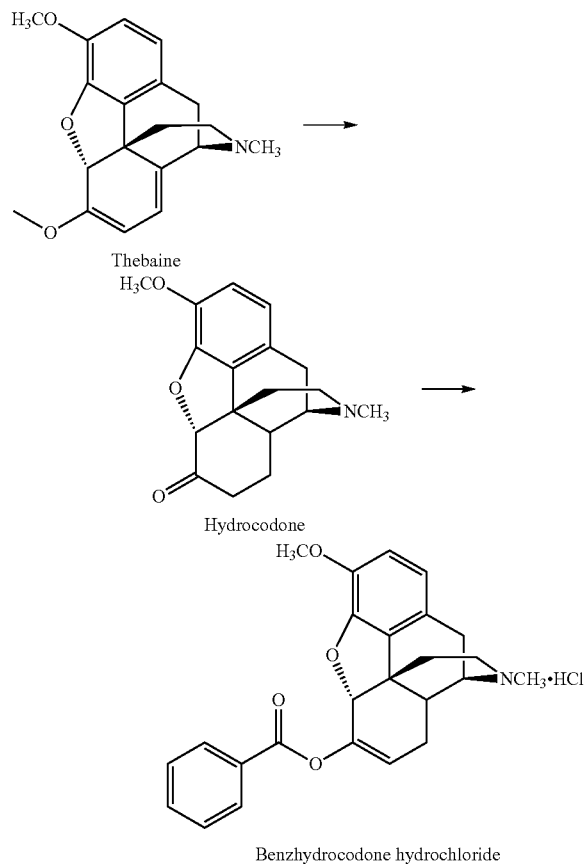

Benzhydrocodone hydrochloride

CPS Thebaine (56.04 g, 155 mmol, 85.9%) and toluene (365 mL) were added to a 2 L 3-necked reactor equipped with distillation head. The resulting mixture was heated up to 80° C.-110° C. to distill off toluene/water (~58 mL). Once distillation was complete, the distillation head was replaced with a cooling condenser. The reaction mixture was cooled to 97° C.-103° C. To a separate 500 mL reactor were added p-TSH (p-Toluenesulfonyl hydrazide) (63.87 g), morpholine (81.0 mL), and toluene (24.0 mL). The resulting mixture was heated to 30° C.-40° C. and held at the temperature for 20-40 minutes. The p-TSH solution was dosed into the thebaine solution over 2.5-3.5 hours at 97° C.-103° C. The reaction mixture was stirred at 97° C.-103° C. for 45-60 minutes and then cooled to 70° C.-80° C. Water (195 mL) and NaOH (50%, 20.0 mL) were added. The resulting mixture was stirred for 30 minutes and allowed to stand for phase separation. The bottom aqueous layer was discarded. The reaction mixture (the toluene/product layer) was adjusted to 50° C.-60° C., and then washed with water (97 mL). The reaction mixture was allowed to stand for phase separation to remove the bottom aqueous layer. The upper layer was cooled to 30° C.-40° C. and then water (158 mL) and $H_2SO_4$ (~96%, 14.4 g) were added. The reaction mixture was stirred for 30 minutes and allowed to stand for phase separation. The upper toluene layer was back-extracted with additional water (41.8 mL) and $H_2SO_4$ (~96%, 3.6 g). The toluene layer was discarded. The two aqueous layers were combined and the pH was adjusted to <1.2 with $H_2SO_4$ (~96%), if needed. The resulting mixture was heated to 85° C.-90° C. and held at the temperature for 2.25-2.75 hours.

Toluene (240 mL) was added once the reaction was complete. The pH of the reaction mixture was adjusted to 9.3-9.7 using NaOH (18%, ~36 g). The reaction mixture was heated to 70° C. and stirred at the temperature for >15 min. The reaction mixture was then allowed to stand for phase separation. The bottom water layer was washed with additional toluene (150 mL) at 70° C. The reaction mixture was allowed to stand for phase separation. The water layer was discarded. The two toluene layers were combined and heated up to distill off water (~15 mL) and toluene (205 mL). The reaction mixture was cooled to 80° C. and benzoic anhydride (200.25 g) was added. The resulting mixture was heated to 115° C.-150° C. while continuing to distill off toluene. The reaction mixture was stirred at 150° C. for additional 5 hours and then cooled to 20° C. The reaction mixture was quenched with toluene (130 mL), acetone (300 mL), and an acid solution made by mixing 37% HCl (13.3 g) with water (252 mL). The reaction mixture was stirred and allowed to stand for phase separation. The upper toluene layer was washed with water (150 mL) and then allowed to stand for phase separation. The two aqueous layers were combined and washed with toluene (150 mL). The upper toluene layer was discarded. The bottom aqueous layer was charged into a 2 L three necked flask equipped with agitation, nitrogen purge, and Dean-Stark apparatus. Toluene (600 mL) was added. The reaction mixture was heated up to 90° C.-110° C. to azeotropically distill off water-toluene until all water was removed from the reaction mixture. The distillation was continued to further remove toluene to a volume of ~100 mL. The reaction mixture was cooled to 20° C. and then filtered. The product was washed with toluene (100 mL×2). The product benzhydrocodone hydrochloride was dried to a constant weight (52.14 g, 77% yield, 96% HPLC purity).

Example 5

Formulation of a Solid, Oral Dosage Form

An oral composition including 100 mg of the compound prepared as in any of Examples 1-4 is formulated with sufficient finely divided lactose to provide a total amount of 580 to 590 mg to fill a size O hard gel capsule.

While the foregoing specification teaches the principles of the invention, with examples provided for the purpose of illustration, it will be understood that the practice of the invention encompasses all of the usual variations, adaptations and/or modifications as come within the scope of the following claims and their equivalents.

A number of patent and non-patent publications may be cited herein in order to describe the state of the art to which this invention pertains. The entire disclosure of each of these publications is incorporated by reference herein.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All methods, compounds, compositions, and formulations described herein that embody the invention can, in alternate embodiments, be more specifically defined by any of the transitional terms "comprising," "consisting essentially of," and "consisting of."

We claim:

1. A process for the preparation of benzhydrocodone comprising the steps of:
   (a) preparing a first mixture comprising benzoic anhydride, hydrocodone free base, and an organic solvent;
   (b) removing a substantial portion of the organic solvent from the first mixture to afford a second mixture; and
   (c) heating the second mixture to a temperature in the range of about 100° C. to about 200° C.

2. The process of claim 1, wherein more than 90% of the organic solvent is removed.

3. The process of claim 1, wherein more than 95% of the organic solvent is removed.

4. The process of claim 1, wherein more than 99% of the organic solvent is removed.

5. The process of claim 1, wherein the organic solvent is selected from the group consisting of toluene, ether, ethyl acetate, and THF.

6. The process of claim 1, wherein the organic solvent is toluene, and wherein the toluene is removed from the reaction mixture by distillation.

7. The process of claim 6, wherein the toluene is removed from the reaction mixture under a flow of $N_2$ gas.

8. A pharmaceutical composition comprising a pharmaceutically acceptable carrier and benzhydrocodone prepared according to the process of claim 1.

9. The process of claim 1, further comprising the step of adding to the mixture a first organic solvent and a solvent which is miscible with both the first organic solvent and water.

10. The process of claim 9, further comprising the step of adding to the mixture an aqueous hydrochloric acid solution.

11. The process of claim 10, further comprising the step of adjusting the pH of the mixture to a pH in the range of from about pH 1.0 to about pH 5.0.

* * * * *